(12) United States Patent
Christopher

(10) Patent No.: US 6,585,642 B2
(45) Date of Patent: Jul. 1, 2003

(54) ENDOSCOPE WITH A REMOVABLE SUCTION TUBE

(75) Inventor: Kent L. Christopher, Denver, CO (US)

(73) Assignee: Evergreen Medical Incorporated, Denver, CO (US)

( * ) Notice: Subject to any disclaimer, the term of this patent is extended or adjusted under 35 U.S.C. 154(b) by 2 days.

(21) Appl. No.: 10/042,656

(22) Filed: Jan. 8, 2002

(65) Prior Publication Data
US 2002/0103419 A1 Aug. 1, 2002

Related U.S. Application Data

(63) Continuation-in-part of application No. 09/618,410, filed on Jul. 18, 2000, now Pat. No. 6,340,344.

(51) Int. Cl.⁷ .............................................. A61B 1/015
(52) U.S. Cl. ........................ 600/156; 600/153; 600/160; 600/182
(58) Field of Search ........................ 600/128, 153–158, 600/160, 182

(56) References Cited

U.S. PATENT DOCUMENTS

| | | | |
|---|---|---|---|
| 4,416,268 A | * 11/1983 | Hagino | 600/132 |
| 4,562,830 A | * 1/1986 | Yabe | 600/155 |
| 4,616,631 A | 10/1986 | Takahashi | |
| 4,646,722 A | 3/1987 | Silverstein et al. | |
| 5,050,585 A | 9/1991 | Takahashi | |
| 5,193,525 A | 3/1993 | Silverstein et al. | |
| 5,257,617 A | 11/1993 | Takahashi | |
| 5,329,940 A | 7/1994 | Adair | |
| 5,349,941 A | 9/1994 | Hori | |
| 5,489,256 A | 2/1996 | Adair | |
| 5,503,616 A | 4/1996 | Jones | |
| 5,685,822 A | 11/1997 | Harhen | |
| 5,746,694 A | 5/1998 | Wilk et al. | |
| 5,876,329 A | 3/1999 | Harhen | |
| 5,938,586 A | 8/1999 | Wilk et al. | |
| 5,944,654 A | 8/1999 | Crawford | |

\* cited by examiner

*Primary Examiner*—John P. Leubecker
*Assistant Examiner*—Henry M. Johnson, III
(74) *Attorney, Agent, or Firm*—Dorr, Carson, Sloan & Birney, P.C.

(57) ABSTRACT

An endoscope has a removable suction tube to facilitate cleaning and reduce the risk of patient infection. The endoscope includes an elongated flexible probe with a housing at its proximal end to control the direction and operation of the probe and for viewing images carried by optical fibers from the distal end of the probe. A recess or slot extending along either the suction tube or probe enables the suction tube to be removably secured to the probe. A suction tube connector at the proximal end of the suction tube allows the suction tube to be removably secured to the housing and also provides a connector for removable attachment to an external suction line. In the preferred embodiment, the suction tube connector includes means for regulating suction through the suction tube, such as a vent opening that can be manually sealed by a healthcare provider.

19 Claims, 6 Drawing Sheets

ENDOSCOPE WITH A REMOVABLE SUCTION TUBE

RELATED APPLICATION

The present application is a continuation-in-part of the Applicant's U.S. patent application Ser. No. 09/618,410, entitled "Endoscope With A Removable Suction Tube," filed on Jul. 18, 2000, now U.S. Pat. No. 6,340,344.

BACKGROUND OF THE INVENTION

1. Field of the Invention

The present invention relates generally to the field of endoscopes. More specifically, the present invention discloses an endoscope with a removable suction tube.

2. Statement of the Problem

Endoscopes have been used for many years in the medical field for viewing within a desired region of the patient's body through the patient's airway, other natural orifices, or a surgical incision. An endoscope typically has an elongated flexible probe with a housing at its proximal end. Optical fibers extending the length of the endoscopic probe carry an image from the distal end of the probe to the housing, where it can be viewed through an eye piece by the physician. The housing also includes one or more controls allowing the physician to direct the distal tip of the probe in a desired direction. The probe can also be equipped with one or more instrument channels for surgical implements. A suction channel extends the length of the endoscopic probe to facilitate removal of mucus, blood, or secretions that can obstruct the physician's view or interfere with endoscopic surgery.

The problem is that these channels are difficult to clean and sterilize because only the ends of the channels are open. A conventional autoclave can be used to sterilize an endoscope probe with heat and pressure. But, this tends to be harmful to the polymer components of the endoscope probe and can substantially shorten its useful life. Alternatively, the endoscope probe can be sterilized by immersion in a liquid chemical bath. Unfortunately, the efficacy of this approaches depends on the ability of the liquid to fully penetrate into all regions of the endoscope probe, which is often not possible if the suction channel contains mucus, coagulated blood, or the like. In addition, neither autoclave sterilization nor chemical bath sterilization can ensure complete removal of biological materials that may become trapped within the channels of an endoscope probe.

One approach has been to manually clean the channels in the endoscope probe with a cleaning rod or brush. However, this approach is relatively labor intensive, costly, and may expose the worker to contamination. There is also a risk that the cleaning process is not 100% effective since it is very difficult to visually inspect the interior length of the channels in the endoscope probe.

3. Prior Art

A variety of endoscopes with removable tubes or sheaths have been disclosed in the prior, including the following:

| Inventor | Patent No. | Issue Date |
|---|---|---|
| Takahashi | 4,616,631 | Oct. 14, 1986 |
| Silverstein et al. | 4,646,722 | Mar. 3, 1987 |
| Takahashi | 5,050,585 | Sep. 24, 1991 |
| Silverstein et al. | 5,193,525 | Mar. 16, 1993 |
| Takahashi | 5,257,617 | Nov. 2, 1993 |
| Adair | 5,329,940 | Jul. 19, 1994 |
| Hori | 5,349,941 | Sep. 27, 1994 |
| Adair | 5,489,256 | Feb. 6, 1996 |
| Jones | 5,503,616 | Apr. 2, 1996 |
| Harhen | 5,685,822 | Nov. 11, 1997 |
| Wilk et al. | 5,746,694 | May 5, 1998 |
| Harhen | 5,876,329 | Mar. 2, 1999 |
| Wilk et al. | 5,938,586 | Aug. 17, 1999 |
| Crawford | 5,944,654 | Aug. 31, 1999 |

The Takahashi '631 patent discloses a removable tube that can be inserted into a slot in an endoscopic probe.

U.S. Pat. No. 4,646,722 to Silverstein et al. discloses an endoscope with a protective sheath having a transparent window at its distal end. Channels for taking biopsies, or injecting air or water to wash the window of the sheath may extend along the endoscope either inside or outside the sheath. If the channels are positioned inside the sheath, they may be inserted in a longitudinal groove formed in the endoscope core.

The Takahashi '585 and '617 patents disclose a sheathed endoscope with a channel tube that is removably insertable into the main body of the endoscopic probe.

U.S. Pat. No. 5,193,525 to Silverstein et al. discloses an endoscope with an antiglare tip at its distal end.

The Adair '940 patent discloses a device for assisting in insertion of an endotracheal tube. The assist device includes a handle, a malleable elongated insertion section, and an endoscope assembly. The handle may also include a suction port for attaching a suction tube for evacuation of the trachea during the intubation process.

Hori discloses an endoscope with a removable cover and an U-shaped viewing channel.

The Adair '256 patent discloses an endoscope with a separable disposable tube assembly.

Jones discloses an endoscope with a collapsible access that allows insertion of functional instruments such as a biopsy device or tubes for supplying air, water, suction, and irrigation.

The Harhen patents disclose an endoscope with an elastomeric sheath.

The patents to Wilk et al. disclose a biopsy channel liner for use with an endoscope.

Crawford discloses an endoscope with a replaceable irrigation channel that is held in a groove extending along the exterior surface of the endoscope.

4. Solution to the Problem

Nothing in the prior art discussed above shows an endoscope with a suction tube that can be removably inserted into a slot extending the length of the endoscope, and having a connector at its proximal end to secure the suction tube to the housing of the endoscope. The suction tube connector can be equipped with a vent hole to allow the physician to regulate suction through the suction tube. The distal end of the suction tube can also be removably attached to a connector within the slot at the distal tip of the endoscope probe.

The present invention overcomes many of the shortcomings of conventional endoscopes by allowing the suction tube to be easily removed and discarded after use. The connectors at either end of the suction tube hold the suction tube securely in place to the remainder of the endoscope. The suction tube tends to prevent biological material from collecting in the slot. However, if cleaning is necessary, the slot is open from the endoscope housing to its distal tip for easy access.

SUMMARY OF THE INVENTION

This invention provides an endoscope having a removable suction tube to facilitate cleaning and reduce the risk of patient infection. The endoscope includes an elongated flexible probe with a housing at its proximal end to control the direction and operation of the probe and for viewing images carried by optical fibers from the distal end of the probe. A recess or slot extending along either the suction tube or probe enables the suction tube to be removably secured to the probe. A suction tube connector at the proximal end of the suction tube allows the suction tube to be removably secured to the housing and also provides a connector for removable attachment to an external suction line. In the preferred embodiment, the suction tube connector includes means for regulating suction through the suction tube, such as a vent opening that can be manually sealed by a healthcare provider.

A primary object of the present invention is to provide an endoscope that is easier to clean and sterilize.

Another object of the present invention is to provide an endoscope that reduces the risk of patient infection.

Yet another object of the present invention is to provide an endoscope that can be quickly and easily assembled and used by healthcare providers.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Structure of the Present Endoscope

Figure 1:
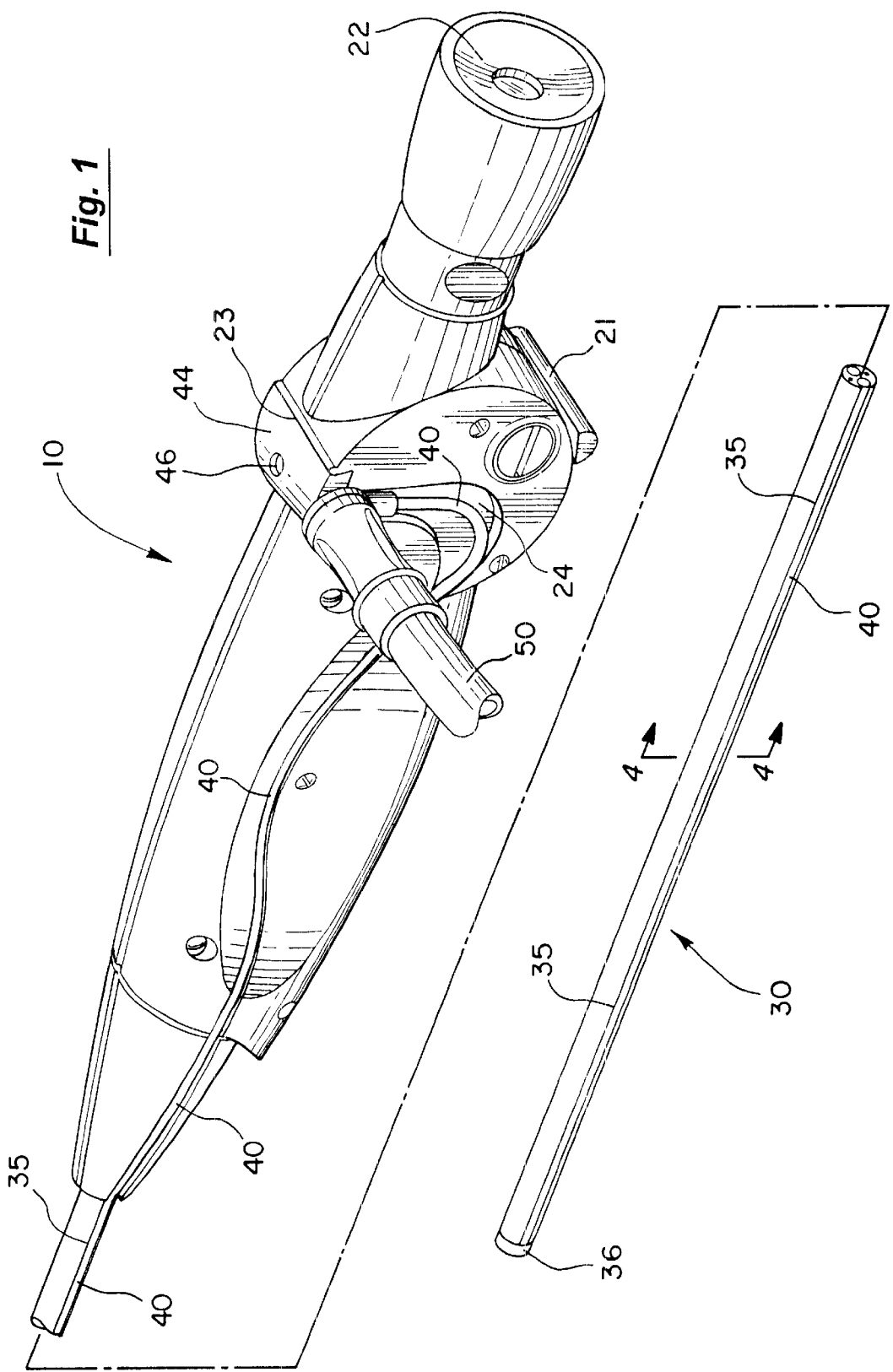
FIG. 1 is a perspective view of the housing 10 and a portion of the flexible probe 30 of the present endoscope.
Figure 2:
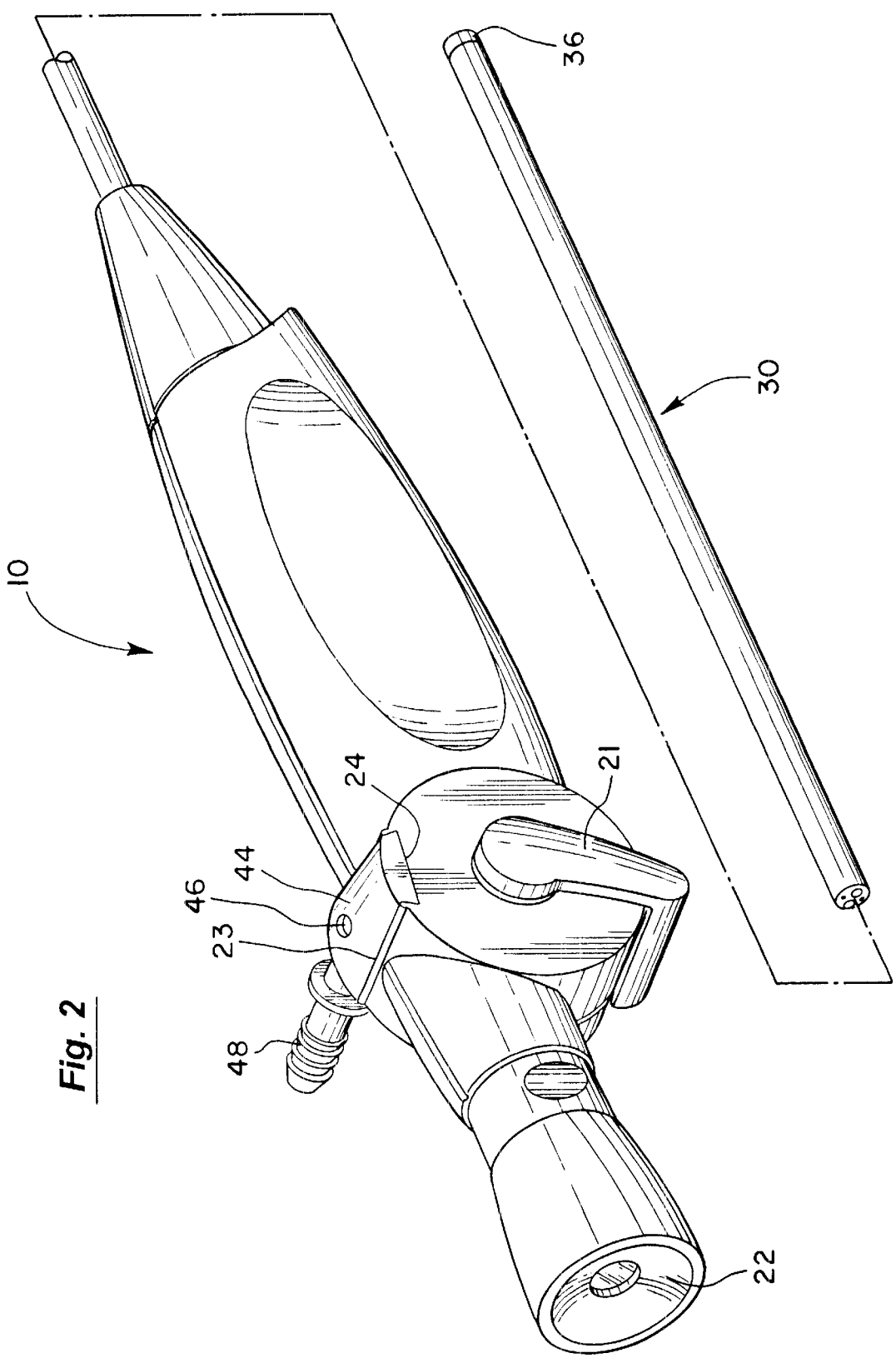
FIG. 2 is a perspective view of the opposing side of the endoscope.

FIG. 1 is a perspective view of the housing 10 and a portion of the flexible probe 30 of the present endoscope. FIG. 2 is a perspective view of the opposing side of the endoscope. As illustrated, the endoscope housing 10 is connected at the proximal end of a flexible probe 30. The housing 10 includes a control lever 21 for controlling the direction of the distal tip of the probe 30, and an eye piece 22 allowing the physician to view the image carried by the probe from its distal tip.

Figure 4:
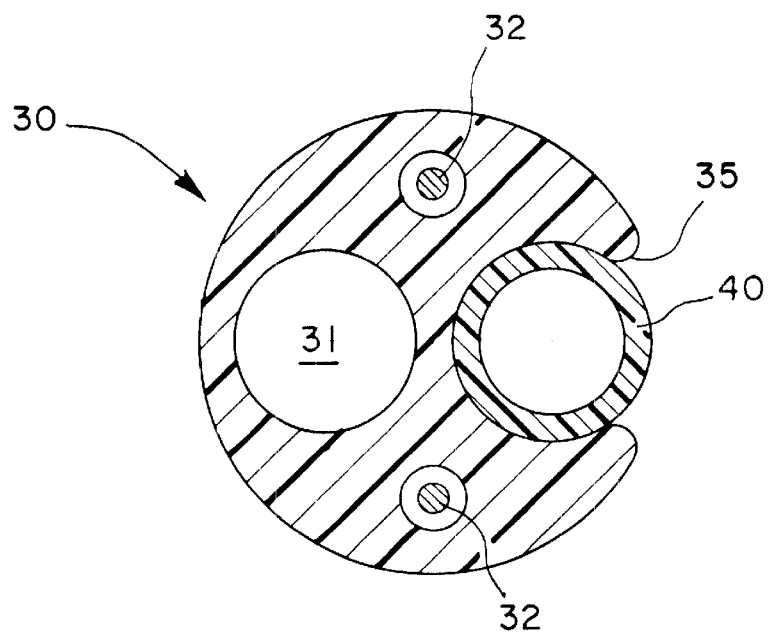
FIG. 4 is a cross-sectional view of the endoscope probe 30.

The flexible probe 30 has an optical fiber channel 31 (shown in FIGS. 4 and 6) containing a plurality of optical fibers extending the length of the probe 30 for carrying light from a light source in the endoscope housing 10 to the distal tip of the probe, and for transmitting images from the distal tip of the probe 30 to the eye piece 22 in the endoscope housing 10. Alternatively, a small camera can be mounted at the distal tip of the probe to capture images that are transmitted by wire to the endoscope housing 10 for viewing. In this embodiment, the probe 30 can still be equipped with optical fibers that carry light from a light source in the endoscope housing 10 to the distal tip of the probe for illumination of the surrounding region. Optionally, the endoscope probe 30 can also have a number of other channels 32 extending along its length for instruments and the like.

In the present invention, a slot 35 extends at least a substantial portion of the length of the probe 30 and at least a portion of the endoscope housing 10, as shown in FIG. 1. In the preferred embodiment, the distal end of the slot 35 is in fluid communication with an opening or port on the distal end of the probe 30, as will be described in greater detail below.

A flexible, disposable suction tube 40 can be removably inserted into the slot 35 with its distal opening adjacent to the distal opening of the slot 35. The slot 35 has a substantially circular cross-section with a diameter sufficient to removably engage the suction tube 40, as depicted in the cross-sectional view of the endoscope probe 30 provided in FIG. 4. Ideally, the suction tube 40 should substantially fill the slot so there is no room for accumulation of biological materials. However, the suction tube 40 should also have a sufficiently small diameter so that it can be manually inserted into the slot 35 and subsequently removed without undue effort by the healthcare provider. Alternatively, the slot 35 can be given a substantially oval cross-section, which might be advantageous in more effectively gripping and retaining the suction tube 40 in the slot 35. The suction tube 40 can be made of any suitable flexible material, such as a polymer, plastic, rubber, or a composite material. The suction tube 40 should be sufficiently rigid to prevent kinking during insertion of the suction tube 40 into the slot 35, and also to prevent collapse of the suction tube 40 under suction. It may be advantageous to fabricate a suction tube that is less rigid and has a softer durometer value at its distal end. In particular, the distal portion of the suction tube 40 must be able to bend along with the distal tip of the probe 30 as it is manipulated by the physician.

The opening along the outside of the slot 35 is formed by the gap between two tapered lips at the outer surface of the probe 30. For example, the surface of the probe 30 can be made of a flexible polymer. These lips should be sufficiently flexible and elastic to allow the suction tube 40 to be manually inserted into the slot 35 without requiring excessive force. After the suction tube 40 has been inserted, the lips return to their original positions and cover a large portion of the outer surface area of the suction tube 40 in the slot 35. This further helps to prevent accumulation of biological material within the slot 35.

Figure 3:
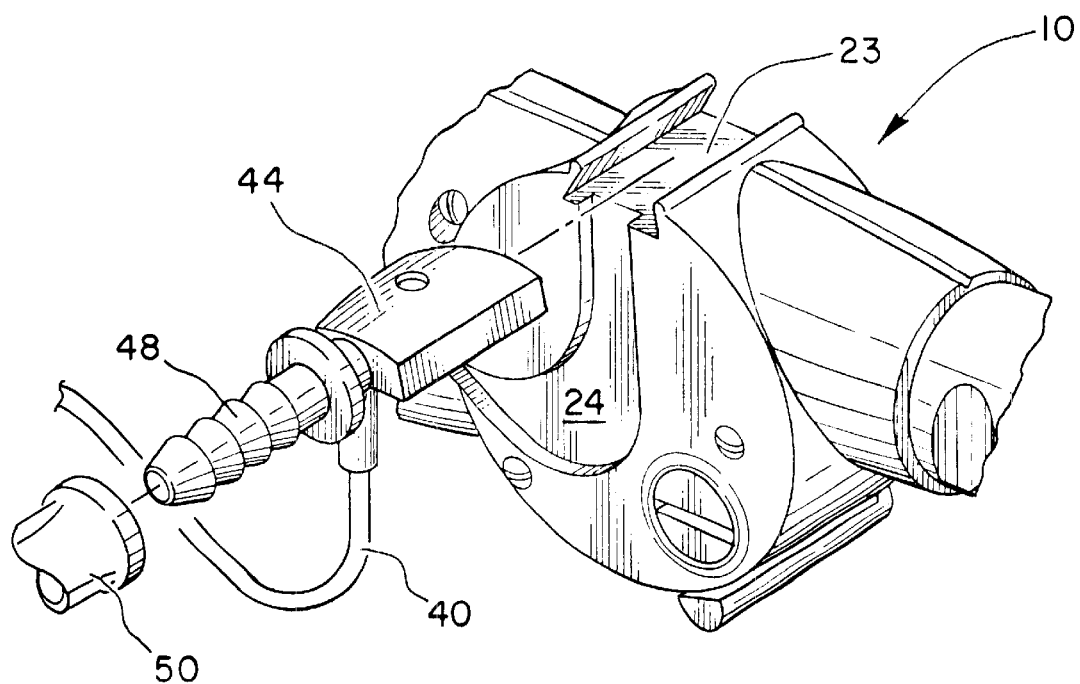
FIG. 3 is a detail exploded view of the suction tube connector 44 and the keyway 23 in the endoscope housing 10.

A suction tube connector 44 is attached at the proximal end of the suction tube 40 as shown in FIGS. 3 and 1. This suction tube connector 44 has an interior airway in communication with the lumen of the suction tube 40 and a vent opening 46 leading from the interior airway to the ambient atmosphere. The physician can manually regulate the degree of suction through the suction tube 40 by placing a finger or thumb over the vent opening 46 on the top of the suction tube connector 44 to control the flow rate of air through the vent opening 46. Alternatively, the vent opening 46 can be located elsewhere along the flow path. For example, a vent opening can be made through the wall of the suction tube 40 itself. A small valve mechanism can also be used for regulating suction through the suction tube. The suction tube connector 44 also can be equipped with a standard port 48 (shown in FIG. 3) for attachment to an external suction line 50, as illustrated in FIG. 1.

One of the primary advantages of the present invention is that it provides a means for securing the suction tube 40 to the endoscope housing 10 as well as the endoscope probe 30. This can be accomplished by a number of means. In the preferred embodiment of the present invention, the endoscope housing 10 includes a connector 23 (e.g., a recessed keyway) that removably secures the suction tube connector 44 to the endoscope housing 10. For example, FIG. 3 is a detail exploded view of the suction tube connector 44 and a keyway 23 in the endoscope housing 10. In this embodiment, two opposing lateral edges of the suction tube connector 44 are sloped to engage the inwardly tapered walls of the housing keyway 23 as the suction tube connector 44 slides into the keyway 23 from the side of the endoscope housing 10. Optionally, a complementary indent and detent on the base of the suction tube connector 44 and the base of the keyway 23 can be used to provide a tactile indication of when the proper degree of insertion has been attained, and to provide a small degree of resistance to prevent the suction tube connector 44 from accidentally sliding out of the keyway 23.

In a minimalist embodiment of the present invention, the opening at the distal end of the suction tube 40 is simply exposed at the distal tip of the endoscope probe 30, which also corresponds to the distal end of the slot 35. However, it would be advantageous to secure the distal end of the suction tube 40 as well as its proximal end to help ensure proper initial installation and prevent the suction tube 40 from sliding along the slot 35 during use of the device. In addition, space constraints or flexibility constraints at the distal tip of the endoscope probe 30 may prevent the suction tube 40 from extending to the distal tip of the endoscope probe 30.

Figure 5:
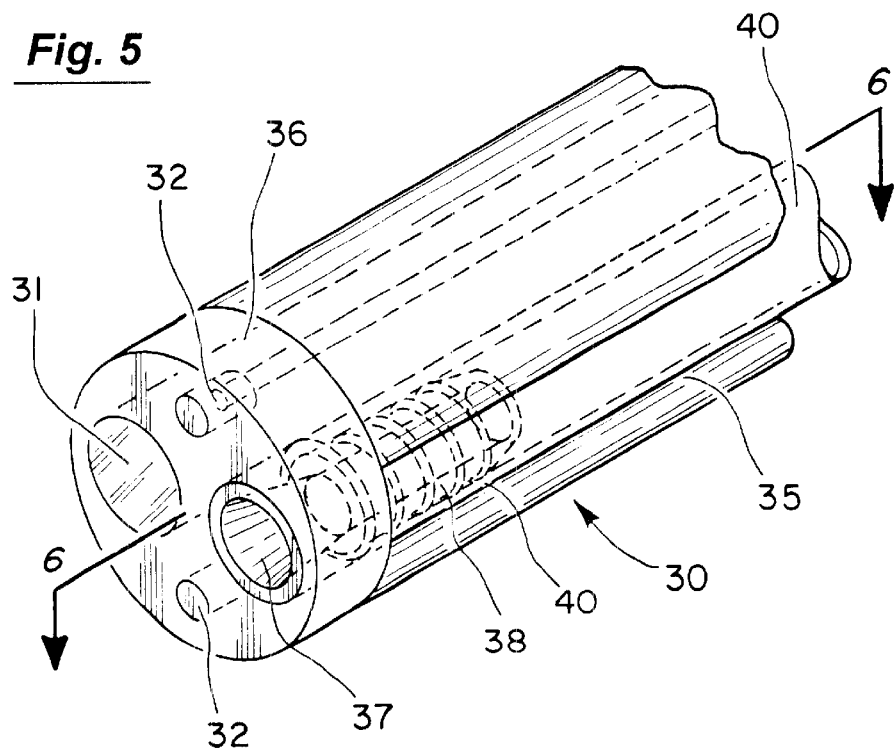
FIG. 5 is a detail perspective view of the distal tip of the endoscope probe 30.
Figure 6:
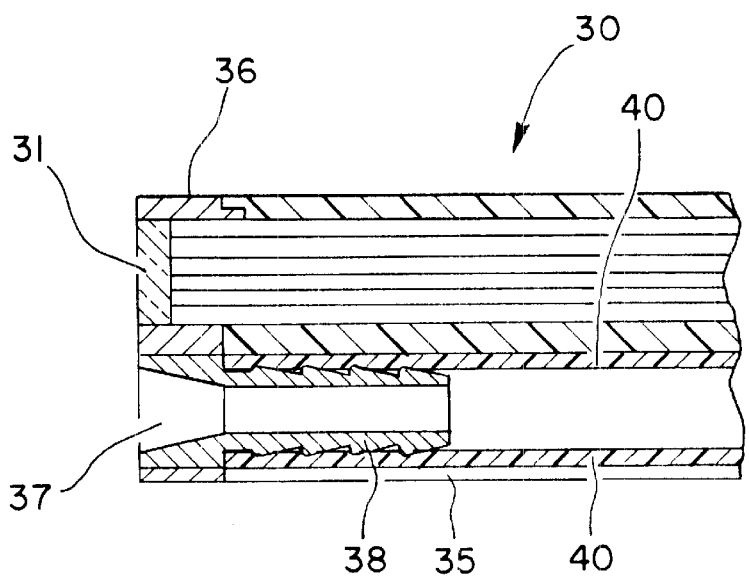
FIG. 6 is a detail cross-sectional view of the distal tip of the endoscope probe 30 corresponding to FIG. 5.

Thus, it may be desirable to provide a second connector 38 at some distance behind the distal tip of the endoscope probe 30 that engages the distal end of the suction tube 40. FIG. 5 is a detail perspective view of the distal tip of this embodiment of the endoscope probe 30. FIG. 6 is a corresponding detail cross-sectional view of the distal tip of the endoscope probe 30. An end plate 36 at the distal tip of the endoscope probe 30 has a number of ports, including a suction opening 37 and a viewing port 31 aligned with the optical fiber channel 31 within the probe 30. The distal connector 38 located within the slot 35 adjacent to the suction opening 37 can be inserted into the distal opening of the suction tube 40 to removably secure the suction tube 40 in fluid communication with the suction opening 37. This configuration provides a complete path for suction of fluid from the region surrounding the distal tip of the probe 30 through the suction opening 37, distal connector 38, suction tube 40, and suction tube connector 44 to the external suction line 50.

With both ends of the suction tube 40 fixed by connectors 44 and 38, it can be difficult to precisely insert the suction tube 40 in the slot 35 without excess or shortfall. To address this potential problem, a portion of the slot 35 on the endoscope housing 10 adjacent to the suction tube connector 44 is widened to serve as a take-up region for the suction tube 40 as illustrated in FIGS. 1 and 3. This widened region 24 of the slot 35 can also accommodate small variations in the length of the suction tube between the connectors 44 and 38.

Method of Use for the Endoscope

Prior to use, the endoscope housing 10 and probe 30 are cleaned and sterilized in the conventional manner. Because the suction tube assembly is designed primarily to be disposable, it would normally be sterilized at the factory and distributed to hospitals and medical offices in sterile packaging. The healthcare provider removes the suction tube assembly from its packaging and inserts the distal end of the suction tube 40 into the slot 35 adjacent to distal tip of the endoscope probe 30. The distal end of the suction tube 40 is advanced distally until it is secured to the distal connector 38 within the slot 35. The remainder of the suction tube 40 is then inserted along the length of the slot 35. The suction tube connector 44 at the proximal end of the suction tube 40 is inserted into the keyway 23 in the endoscope housing 10 to secure the other end of the suction tube in place. A suction line 50 is then attached to the corresponding suction port 48 on the suction tube connector 44.

After initial preparation of the endoscope is complete, it can be inserted into the patient for viewing. The physician controls the direction of the probe tip using the control lever 21. Suction is supplied through the external suction line 50 and the suction tube 40. The amount of suction can be regulated by the physician via the vent opening 46.

After use, the external suction line 50 is disconnected from the suction port 48 and the suction tube connector 44 is detached from the endoscope housing 10. The suction tube 40 is stripped out of the slot 35 and detached from the distal connector 38. The entire suction tube assembly can then be discarded. The endoscope housing and probe can be cleaned and sterilized for subsequent reuse. If necessary, a small brush can be employed to clean any matter accumulating in the slot 35.

Alternative Embodiment of the Suction Tube and Endoscope Probe

Figure 7:
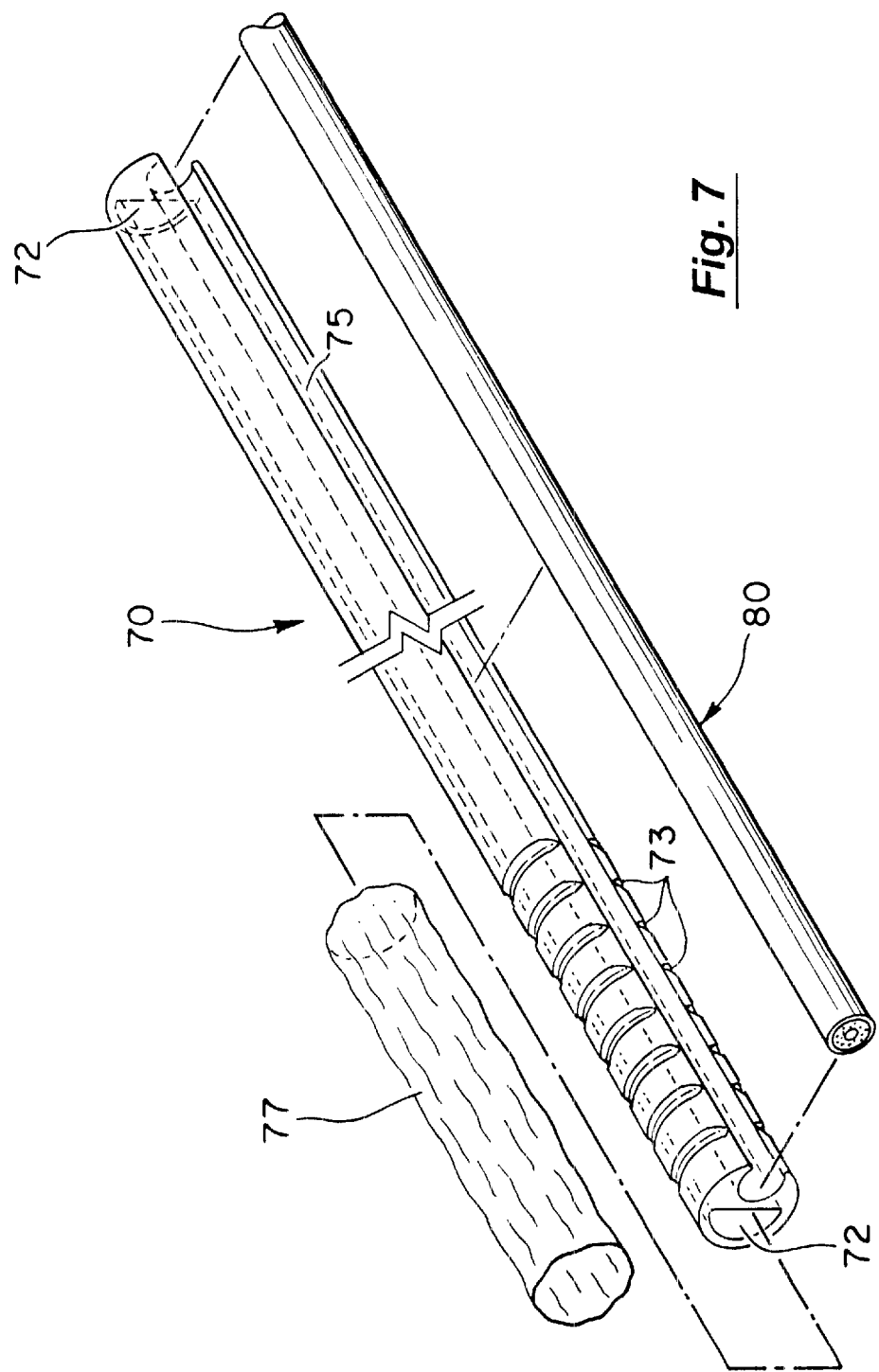
FIG. 7 is an exploded perspective view of an alternative embodiment of the suction tube 70 and endoscope probe 80.
Figure 8:
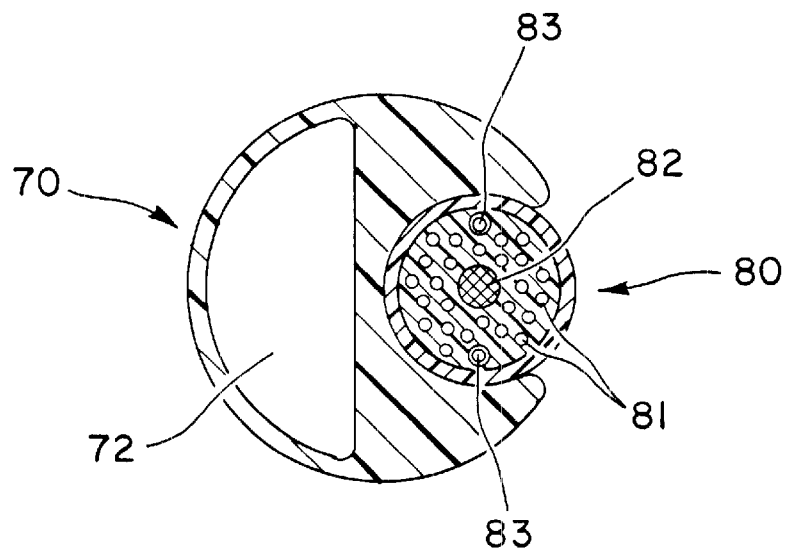
FIG. 8 is a cross-sectional view of the suction tube 70 and endoscope probe 80 corresponding to FIG. 7.
Figure 9:
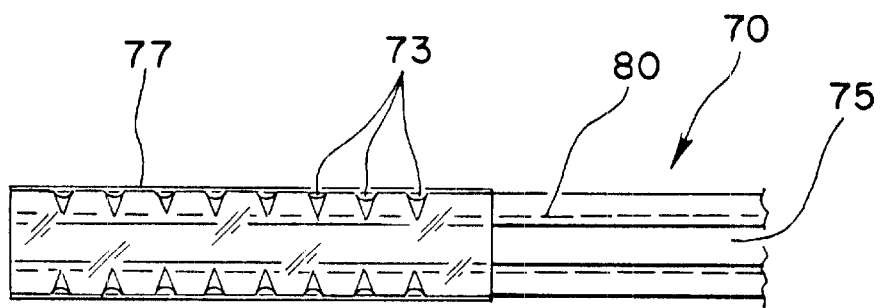
FIG. 9 is a cross-sectional view of the distal tip of the endoscope probe.

FIGS. 7–9 show an alternative embodiment of the present invention in which the suction tube 70 clips over the endoscope probe 80, rather than being inserted into a recess in the endoscope probe as shown in the previous embodiment. FIG. 7 is an exploded perspective view of this embodiment of the suction tube 70 and endoscope probe 80. FIG. 8 is a cross-sectional view of the suction tube and endoscope probe corresponding to FIG. 7.

This embodiment allows the present invention to be used in conjunction with any conventional endoscope probe 80 having the appropriate cross-sectional shape and diameter. As before, the endoscope probe 80 has light fibers 81, fiber optics 82, and a number of wires 83 for controlling the direction of the distal tip of the endoscope probe 80.

The suction tube 70 has a suction lumen 72 extending along its entire length, and a recess 75 that extends along at least the distal portion of the suction tube 70. This recess is used to removably secure the suction tube 70 to the endoscope probe 80. For example, the recess 75 can have a substantially circular cross-section with an opening that clips around the probe 80, as illustrated in FIG. 7. Alternatively, the recess could have a cross-section suitable for gripping or slipping over the endoscope probe 80. The suction tube 70 could also be formed with a series of discrete fasteners that removably engage the endoscope probe 80 at intervals along its length.

A suction tube connector is attached at the proximal end of the suction tube 70, as previously discussed, and can be equipped with an opening to regulate suction. Alternatively, other means can be provided for regulating suction through the suction tube 70, such as an opening in the suction tube 70 that can be manually sealed by the thumb or finger of a healthcare provider, or a small valve could be employed for this purpose The proximal end of the suction tube 70 can be bonded to a port on the suction tube connector that fits over the outside diameter of the suction tube 79, Alternatively, an adaptor can be provided as a transition between the half-moon shaped cross-section of the suction lumen 72 and suction tube connector.

The distal tip of the suction tube 70 can be equipped with a series of notches 73 to facilitate bending and provide an enhanced range of motion for the distal portion of the suction tube 70. These notches 73 are spaced at intervals along both sides of the distal portion of the suction tube 70 in the plane of motion for the endoscope probe 80. A flexible sheath or sleeve 77 can be extended over the distal tip of the suction tube 70 to cover the notches 73 and prevent the accumulation of matter in the notches, as shown in the cross-sectional view of the distal tip of the assembly in FIG. 9. The sheath 77 also helps to secure the suction tube 70 to the endoscope probe 80. For example, the sheath 77 can be made a thin, flexible layer of polymer.

The above disclosure sets forth a number of embodiments of the present invention. Other arrangements or embodiments, not precisely set forth, could be practiced under the teachings of the present invention and as set forth in the following claims.

I claim:

1. An endoscope comprising:
    an elongated flexible probe having a proximal end and a distal end with optical fibers carrying images from the distal end of the probe;
    a housing attached at the proximal end of the probe controlling the direction and operation of the probe;
    a suction tube having a recess extending along the suction tube to removably secure the probe to the suction tube; and
    a suction tube connector at the proximal end of the suction tube removably securable to the housing and having a connector for removable attachment to an external suction line.

2. The endoscope of claim 1 further comprising means for regulating suction through the suction tube.

3. The endoscope of claim 2 wherein said means for regulating suction comprises an opening in the suction tube that can be manually sealed by a healthcare provider to regulate suction through the suction tube.

4. The endoscope of claim 2 wherein the means for regulating suction comprises an opening in the suction tube connector that can be manually sealed by a healthcare provider to regulate suction through the suction tube.

5. The endoscope of claim 1 wherein the recess has a substantially circular cross-section with an opening that clips around the probe.

6. The endoscope of claim 1 wherein the housing further comprises a housing connector, and the suction tube connector is removably securable to the housing connector.

7. The endoscope of claim 1 wherein the housing further comprises a keyway and the suction tube connector is removably securable to the keyway.

8. The endoscope of claim 1 further comprising a plurality of notches spaced along the distal portion of the suction tube to provide an enhanced range of motion for the distal portion of the suction tube.

9. The endoscope of claim 8 further comprising a flexible sheath covering the notches and the distal portion of the suction tube.

10. An endoscope comprising:
    an elongated flexible probe having a proximal end and a distal tip with optical fibers carrying images from the distal tip of the probe;
    a housing attached at the proximal end of the probe controlling the direction and operation of the probe, said housing having a housing connector;
    a suction tube having a recess extending along the suction tube, said probe being insertable into the recess to removably secure the probe to the suction tube; and
    a suction tube connector at the proximal end of the suction tube removably securable to the housing connector and having:
        (a) a connector for removable attachment to an external suction line for supplying suction through the suction tube; and
        (b) an opening that can be manually sealed by a healthcare provider to regulate suction through the suction tube.

11. The endoscope of claim 10 wherein the housing connector comprises a keyway and the suction tube connector is removably securable to the keyway.

12. The endoscope of claim 10 wherein the recess has a substantially circular cross-section with an opening that clips around the probe.

13. The endoscope of claim 10 further comprising a plurality of notches spaced along the distal portion of the suction tube to provide an enhanced range of motion for the distal portion of the suction tube.

14. The endoscope of claim 13 further comprising a flexible sheath covering the notches and the distal portion of the suction tube.

15. An endoscope comprising:
    an elongated flexible probe having a proximal end and a distal end with optical fibers carrying images from the distal end of the probe;
    a housing attached at the proximal end of the probe controlling the direction and operation of the probe, said housing having a housing connector;
    a suction tube having a recess extending along the suction tube, said probe being removably insertable into the recess on the suction tube to removably secure the probe to the suction tube, said suction tube also having a plurality of notches spaced along the distal portion of the suction tube to provide an enhanced range of motion for the distal portion of the suction tube; and
    a suction tube connector at the proximal end of the suction tube removably securable to the housing connector, said suction tube connector having a connector for removable attachment to an external suction line for supplying suction through the suction tube.

16. The endoscope of claim 15 wherein the housing connector comprises a keyway and the suction tube connector is removably securable to the keyway.

17. The endoscope of claim 15 wherein the recess has a substantially circular cross-section with an opening that clips around the probe.

18. The endoscope of claim 15 further comprising a flexible sheath covering the notches and the distal portion of the suction tube.

19. The endoscope of claim 15 further comprising an opening in the suction tube connector that can be manually sealed by a healthcare provider to regulate suction through the suction tube.

* * * * *